United States Patent [19]

Reuther et al.

[11] 4,260,532

[45] Apr. 7, 1981

[54] AQUEOUS ISOCYANATE EMULSIONS PREPARED WITH POLYGLYCOL AND POLYMERIZED UNSATURATED ACID AMIDE

[75] Inventors: Wolfgang Reuther, Heidelberg; Adolph Segnitz, Bad Durkheim; Otto Wittmann, Frankenthal; Hermann Schatz, Neustadt, all of Fed. Rep. of Germany

[73] Assignee: BASF Aktiengesellschaft, Ludwigshafen, Fed. Rep. of Germany

[21] Appl. No.: 56,525

[22] Filed: Jul. 11, 1979

[30] Foreign Application Priority Data

Jul. 19, 1978 [DE] Fed. Rep. of Germany ....... 2831674

[51] Int. Cl.³ .................... C08L 33/24; C08L 39/06

[52] U.S. Cl. ...................... 260/29.6 HN; 260/29.2 N; 260/29.6 N; 260/29.6 NR; 260/29.6 E; 260/29.6 H; 525/424; 526/342

[58] Field of Search ................. 260/29.6 HN, 29.6 N, 260/29.2 N; 528/342; 525/424

[56] References Cited

U.S. PATENT DOCUMENTS

| | | | |
|---|---|---|---|
| 3,401,135 | 9/1966 | Sato | 260/29.6 N |
| 3,931,088 | 1/1976 | Sakurada et al. | 260/29.6 N |

*Primary Examiner*—Harold D. Anderson
*Attorney, Agent, or Firm*—Norbert M. Lisicki; David L. Hedden

[57] ABSTRACT

Aqueous polyisocyanate emulsions are prepared by employing water-soluble polyamides as emulsification agents.

4 Claims, No Drawings

AQUEOUS ISOCYANATE EMULSIONS PREPARED WITH POLYGLYCOL AND POLYMERIZED UNSATURATED ACID AMIDE

BACKGROUND OF THE INVENTION

1. Field of the Invention

The invention concerns a process for the manufacture of aqueous polyisocyanate emulsions. More particularly, the invention concerns an improvement in the process for the manufacture of aqueous polyisocyanate emulsions wherein water-soluble polyamides are employed as emulsification agents.

2. Description of the Prior Art

The use of isocyanates as chipboard adhesive is well known. Particularly well known are binders based on diphenylmethane-4,4'-diisocyanate. As solvent-free liquid products, they can be used in the processing facilities employed in the wood industry.

One drawback, particularly in the case of low concentrations, is that it is difficult to distribute the isocyanate-based adhesives uniformly on the chip material. This can cause a variation in the properties of the finished chipboard. Another drawback is that vessels and-/or machines contaminated with isocyanate cannot be cleaned simply with water. It is known that organic solvents can be used to dilute isocyanates. However, suitable solvents such as dichloromethane and others cannot be used for toxicological reasons and other solvents such as acetals are not practical because of the fire hazard.

In German Published Application No. 2,610,552, the use of aqueous emulsions of isocyanates as adhesives for lignocellulose-containing particles was suggested.

However, special requirements must be met by the isocyanates themselves and the emulsifying auxiliaries as indicated by the result of the experiments treated in the German Published Application. Prepolymers, that is, reaction products of polyisocyanates with polyester and/or polyether polyols, which still have reactive isocyanate end groups are preferably used as (poly)-isocyanates. Nonionic products free of reactive hydroxyl-, amino- or carboxylic ester groups are used as emulsifiers and/or surface active agents.

As the German Published Application admits, however, even with the use of considerable quantities of special hydrophobic polyols which are used for the manufacture of the above-referenced prepolymers, it is not possible to obtain emulsions which have a sufficient service life. Example 2 of the German Published Application indicates that the loss of isocyanate groups in the emulsion during two hours at room temperature is approximately 14 to 17 percent in the most favorable case and more than 50 percent in the less favorable case.

For the expert engaged in the manufacture of wooden products, this means that such an adhesive is without practical value since the required service life between mixing an emulsion and use, which is based on the capacity of the storage vessels for adhesive and adhesive-coated chip goods, cannot be achieved.

German Patent Application No. P 2703271 is directed to a process of manufacturing aqueous, storage-stable polyisocyanates wherein the polyisocyanates are dispersed and/or emulsified in water in the presence of an emulsifier based on a polyglycol having a molecular weight of approximately 4,000 to 20,000. There is no teaching in the prior art of the use of water-soluble polyamides as emulsifiers for aqueous polyisocyanate solutions.

The purpose of this invention, therefore, lies in creating isocyanate preparations which either do not have the referenced drawbacks or display them to a considerably lesser degree. More specifically, the purpose of this invention is the creation of improved storage-stable aqueous emulsions of polyisocyanates.

BRIEF SUMMARY OF THE INVENTION

This invention concerns an improvement in the process for the manufacture of aqueous polyisocyanate emulsions. Emulsions prepared by employing a polyglycol of molecular weight 4,000 to 20,000 may be prepared by partially or totally replacing the polyglycol with a water-soluble polyamide.

DESCRIPTION OF THE PREFERRED EMBODIMENT

The instant invention is directed to an improvement in the process of manufacturing aqueous polyisocyanate emulsions by partially or totally replacing the polyglycols by a water-soluble polyamide (for instance polyvinyl pyrrolidone) obtained by the polymerization of an olefinically unsaturated acid amide, resulting in aqueous emulsions of isocyanate which have an increased service life, and, if desired, have a higher concentration of isocyanate and, in addition to this, are cheaper since less emulsifier is required for their manufacture.

In general, a concentration of 0.5 to 5 percent of a polyamide such as polyvinyl pyrrolidone based on the total weight of the emulsions suffices to produce a stable emulsion in which the titratable isocyanate content does not decrease by more than approximately 1 percent in 10 hours. This is shown in Table I below.

Polyvinyl pyrrolidone having a range of molecular weights of 20,000 to 1,000,000 is suitable for the purpose of the invention. The concentration of polyvinyl pyrrolidone may vary depending on the molecular weight.

Other useful polymeric carboxylic amides are those which are obtained by the traditional polymerization of olefinically unsaturated monomers include the polymers of vinyl caprolactam, of acrylamide, of methacrylamide. In part, they may also be obtained by polymer homologous reaction of other vinyl polymerizates, for instance, from polyacrylonitrile.

In some cases, the use of a mixture of several emulsifiers is advantageous. Protective colloids may also be employed. In certain cases, it is uncertain (upon application of several emulsifying agents) which one of the agents is to be considered as an emulsifier and which one as a protective colloid. It should be understood that even the use of small effective quantities of the polyamide together with another emulsifying agent which may also be present in greater quantities is covered by the invention.

Examples of organic polyisocyanates which can be used for the process according to this invention are aromatic isocyanates, in particular diisocyanates such as m- and p-phenylene diisocyanate, 2,4- and 2,6-toluenediisocyanate, diphenylmethane-4,4'-diisocyanate, 2,4-chlorophenylenediisocyanate, 1,5-naphthalenediisocyanate, diphenylene-4,4'-diisocyanate, 4,4'-diisocyanate-3,3'-dimethyldiphenyl, 3-methyldiphenylmethane-4,4'-diisocyanate, diphenyletherdiisocyanate and triisocyanates such as 2,4,6-triisocyanatotoluene and 2,4,4'-triisocyanatodiphenylether. These are generally obtained by phosgenating corresponding amines as is well known to those skilled in the art. Mixtures of isocyanates include, for instance, the commercially available mixtures of 2,4- and 2,6-isomers of toluene diisocyanate as well as the mixtures of di- and/or higher polyisocyanates which are produced by phosgenation of aniline-formaldehyde condensates. Such mixtures are generally known and they include the crude phosgenation products which contain mixtures of methylene bridge-containing polyphenyl polyisocyanates including diisocyanates, triisocyanates, and higher polyisocyanates together with the phosgenation byproducts.

Preferred polyisocyanates which may be used in accordance with this invention are those wherein the isocyanate is an aromatic diisocyanate or polyisocyanates with higher functionality, in particular, crude mixtures of methylene bridge-containing polyphenyl polyisocyanates, which contain diisocyanates, triisocyanates or polyisocyanates with higher functionality. Methylene bridge-containing polyphenyl polyisocyanates are generally known and they have the general formula

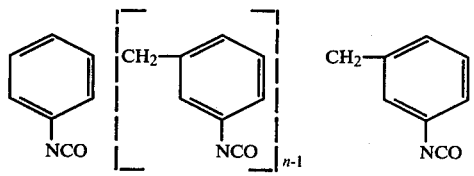

wherein n is more than 1 and in the case of crude mixture, represents an average of more than 1. These compounds are produced by phosgenation of corresponding mixtures of polyamines obtained by the condensation of aniline and formaldehyde. It is customary to refer to crude mixtures of methylene bridge-containing polyphenyl polyisocyanates containing diisocyanates, triisocyanates and polyisocyanate with higher functionalities as MDI.

Less suited organic isocyanates which may be used according to the invention are isocyanate radical-containing prepolymers which are produced by reacting an excess of diisocyanate or a polyisocyanate with higher functionalities with a polyester containing free hydroxyl groups or a polyether containing free hydroxyl groups as well as products which are obtained by the reaction of an excess of diisocyanate or polyisocyanate of higher functionality with monomeric glycols or a mixture of monomeric glycols such as ethylene glycol, trimethylolpropane and butanediol.

The prior art teaches that higher molecular weight polyglycols, particularly polyethylene glycols, polypropylene glycols, as well as mixed glycols with molecular weights between 4,000 and 20,000, preferably between 6,000 and 12,000, are suitable emulsifiers for the manufacture of the emulsions of polyisocyanates.

A typical emulsion is obtained in the following manner from 30 parts of diphenylmethane-4,4'-diisocyanate, 10 parts of polyethylene glycol and 60 parts of water:

The polyethylene glycol (average molecular weight 9,000, for instance, the BASF Product available under the trade name of Pluriol E 9000) is dissolved in 60 parts of water and is stirred into the agitated solution of diphenylmethane-4,4'-diisocyanate (for example, Kauramat CE 5043 by BASF AG). The emulsification by means of a high speed agitator (for example, Tornado or Turrax) requires approximately 10 to 30 seconds.

The stability of the isocyanate emulsion can be measured by titration using bromophenol blue as the indicator. For this purpose, samples of the emulsions taken at certain intervals, are mixed with excess dibutylamine solution, and the unreacted amine is back titrated with methanolic hydrochloric acid. Comparison is then made against a titration of pure polyisocyanate.

The process according to the invention is illustrated by the following examples:

EXAMPLE 1

A typical emulsion consisting of 50 parts of technical grade diphenylmethane-4,4'-diisocyanate (MDI) and 50 parts of 4 percent aqueous emulsifier solution is prepared in the following manner:

A 4 percent aqueous solution of the polyvinyl pyrrolidone is produced by dissolving polyvinyl pyrrolidone (for example the material available under the trade name Luviskol K 90) in warm water. Diphenylmethane-4,4'-diisocyanate is stirred into the cooled solution. The emulsification requires mixing approximately 10 to 30 seconds using a high speed mixer.

In order to determine the stability of the emulsion, the isocyanate content at the point of manufacture is measured as 100 percent and the reduction is measured continuously. The emulsions are essentially stable over a 7 hour period. The variations lie within the error limit of the measuring method.

TABLE I

| 50 Parts diisocyanate 50 parts 4 percent Luviskol solution | |
|---|---|
| Hours | Isocyanate (%) relative to 0 time |
| 0 | 100.0 |
| 1 | 100.6 |
| 2 | 100.0 |
| 3 | 99.4 |
| 4 | 99.4 |
| 5 | 98.7 |
| 6 | 100.0 |
| 7 | 99.4 |

EXAMPLE 2

An emulsion is produced as follows from 50 parts of technical grade diphenylmethane-4,4'-diisocyanate (MDI) and 50 parts 1 percent aqueous emulsifier solution:

A 1 percent aqueous solution of an emulsifier-protective colloid system is produced by dissolving polyethylene glycol (for example the material commercially available under the tradename Pluriol E 9000) and polyvinyl pyrrolidone (for example the product commercially available under the tradename Luviskol K 90) in a weight ratio of 19:1 in warm water. Diphenylmethane-4,4'-diisocyanate is stirred into the cooled solution. The emulsification requires mixing approximately 10 to 30 seconds using a high speed agitator.

In order to determine the stability of the emulsion, the isocyanate content at the point of manufacture is set equal to 100 percent and the reduction is measured continuously. The emulsions do not show any loss of isocyanate activity within the measuring error over a 9 hour period.

TABLE II

| | 50 Parts diisocyanate 50 Parts 1 percent emulsifier - protective colloid solution |
|---|---|
| Hours | Isocyanate (%) relative to 0 time |
| 0 | 100.0 |
| 1 | 100.6 |
| 2 | 100.0 |
| 3 | 100.0 |
| 4 | 100.0 |
| 5 | 99.4 |
| 6 | 98.1 |
| 7 | 100.0 |
| 8 | 99.4 |
| 9 | 99.4 |

EXAMPLE 3

As described above, an emulsion is produced using a 3 percent aqueous emulsifier solution. The 3 percent aqueous emulsifier solution was prepared by dissolving polyethylene glycol and polyvinyl-epsilon-caprolactam, commercially available under the trade name of Lubasin S in a weight ratio of 30:1 at room temperature in a corresponding quantity of water.

Emulsions of 50 parts diphenylmethane-4,4'-diisocyanate and 50 parts of the 3 percent aqueous emulsifier solution do not show any measurable drop in the isocyanate content for a period of 6 hours.

EXAMPLE 4

Pine chips produced under pilot plant conditions and having a moisture content of approximately 4 percent are treated with the emulsion of Example 1 and the same emulsion at a concentration of 40 percent. The emulsion is distributed on the chips in such a manner that two to four percent isocyanate reaches the wood. For comparative purposes, the wood chips are also treated with non-emulsified isocyanate.

The pretreated wood chips are formed into a chip cake in a test shaker. The pressing temperature is 165° C. with a pressing time of 4 minutes and a specific pressure of 2.5 N/mm². Release papers are employed in order to prevent undue sticking. The thickness of the finished chipboards is 18.5 millimeters and the density is approximately 610 kilograms per cubic meter. The panels are tested according to DIN 52 360-65.

TABLE III

| | Isocyanate | 40% Emulsion | 50% Emulsion |
|---|---|---|---|
| Panel Test according to DIN 52 360-65 | 30.7 | 31.1 | 32.1 |
| Resistance to transfer stress V 20 (N/mm²) | 0.78 | 1.02 | 1.02 |
| Resistance to transfer stress V 100 (N/mm²) | 0.23 | 0.30 | 0.28 |
| Swelling after 2 hours (%) | 4.1 | 4.3 | 4.2 |
| Swelling after 24 hours (%) | 17.1 | 16.3 | 16.3 |

The embodiments of this invention in which an exclusive privilege or property is claimed are:

1. In the process for the manufacture of aqueous polyisocyanate emulsions wherein said polyisocyanate is emulsified in the presence of a polyglycol, the improvement comprises replacing said polyglycol partially or wholly with a water-soluble polymeric amide obtained by the polymerization of an olefinically unsaturated acid amide.

2. The process of claim 1 wherein said amide is polyvinyl pyrrolidone.

3. The process of claim 1 wherein the concentration of said amide is from 0.5 to 5 weight percent based on the total weight of the emulsion.

4. The process of claim 1 wherein said polyisocyanate is the phosgenated product of the condensation of aniline and formaldehyde.

* * * * *